United States Patent [19]

Peterson

[11] 4,124,621

[45] Nov. 7, 1978

[54] CIS-4,5-DIDEHYDRO-12,13(E)-DIDEHYDRO-13,14-DIHYDRO-9-DEOXY-PGD$_1$ COMPOUNDS

[75] Inventor: David C. Peterson, Portage, Mich.

[73] Assignee: The Upjohn Company, Kalamazoo, Mich.

[21] Appl. No.: 809,263

[22] Filed: Jun. 23, 1977

Related U.S. Application Data

[62] Division of Ser. No. 614,244, Sep. 17, 1975, and Ser. No. 809,248, Jun. 23, 1977, Pat. No. 4,099,014, which is a division of said Ser. No. 614,244.

[51] Int. Cl.$^2$ ............................................. C07C 121/00
[52] U.S. Cl. ..................................... 260/413; 260/408; 260/410; 260/410.5; 260/410.9 R; 560/121; 562/503
[58] Field of Search .................. 260/514 D, 408, 410, 260/410.5, 410.9 R, 143; 560/121

[56] References Cited

U.S. PATENT DOCUMENTS

| 3,878,239 | 4/1975 | Hayashi et al. | 260/514 |
| 4,016,184 | 4/1977 | Morton et al. | 260/408 |

Primary Examiner—Robert Gerstl
Attorney, Agent, or Firm—Robert A. Armitage

[57] ABSTRACT

Prostaglandin analogs with the following cyclopentane ring structure:

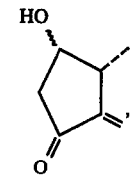

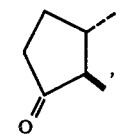

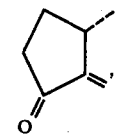

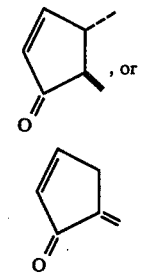

, or

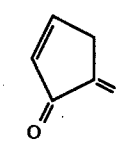

are disclosed along with intermediates useful in their preparation and processes for their preparation. These analogs are useful for some of the same pharmacological purposes as the prostaglandins, particularly and especially as blood platelet aggregation inhibitors.

12 Claims, No Drawings

CIS-4,5-DIDEHYDRO-12,13(E)-DIDEHYDRO-13,14-DIHYDRO-9-DEOXY-PGD$_1$ COMPOUNDS

The present application is a divisional application of Ser. No. 614,244, filed Sept. 17, 1975, now pending. U.S. Ser. No. 809,248, filed June 23, 1977, and also a divisional application of said Ser. No. 614,244, has now issued as U.S. Pat. No. 4,099,014.

The present invention relates to prostaglandin analogs, for which the essential material constituting disclosure therefor is incorporated by reference here from U.S. Pat. No. 4,099,014.

I claim:

1. A prostaglandin analog of the formula

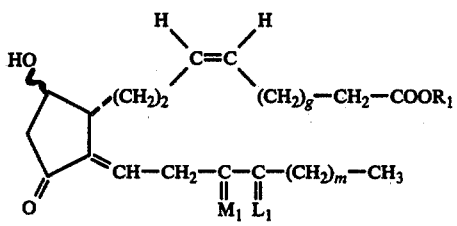

wherein $m$ is one to 5, inclusive;
wherein $M_1$ is

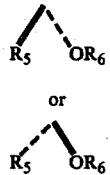

or

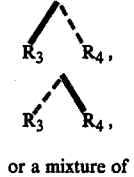

wherein $R_5$ and $R_6$ are hydrogen or methyl, with the proviso that one of $R_5$ and $R_6$ is methyl only when the other is hydrogen;
wherein $L_1$ is

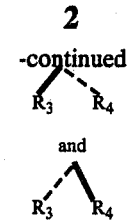

or a mixture of

and

wherein $R_3$ and $R_4$ are hydrogen, methyl, or fluoro, being the same or different, with the proviso that one of $R_3$ and $R_4$ is fluoro only when the other is hydrogen or fluoro;

wherein $R_1$ is hydrogen, alkyl of one to 12 carbon atoms, inclusive, cycloalkyl of 3 to 10 carbon atoms, inclusive, phenyl, phenyl substituted with one, two, or three chloro or alkyl of one to 3 carbon atoms, inclusive, or a pharmacologically acceptable cation; and wherein $g$ is one, 2, or 3.

2. A compound according to claim 1, wherein $M_1$ is

3. A compound according to claim 1, wherein $M_1$ is

4. A compound according to claim 3, wherein $m$ is 3.
5. A compound according to claim 4, wherein $g$ is 3.
6. 2a-2b-Dihomo-cis-4,5-didehydro-13,14-dihydro-12,13(E)-didehydro-9-deoxy-PGD$_1$, a compound according to claim 5.
7. A compound according to claim 4, wherein $g$ is one.
8. A compound according to claim 7, wherein $R_5$ and $R_6$ are both hydrogen.
9. A compound according to claim 8, wherein $R_3$ and $R_4$ are both hydrogen.
10. cis-4,5-Didehydro-13,14-dihydro-12,13(E)-didehydro-9-deoxy-PGD$_1$, a compound according to claim 9.
11. A compound according to claim 8, wherein $R_3$ and $R_4$ are both fluoro.
12. 16,16-Difluoro-cis-4,5-didehydro-13,14-dihydro-12,13(E)-didehydro-9-deoxy-PGD$_1$, a compound according to claim 11.

* * * * *

UNITED STATES PATENT OFFICE
CERTIFICATE OF CORRECTION

Patent No. 4,124,621            Dated November 7, 1978

Inventor(s)  David C. Peterson

It is certified that error appears in the above-identified patent and that said Letters Patent are hereby corrected as shown below:

Column 1, lines 18-25, that portion of the formula reading                          should read

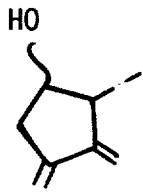             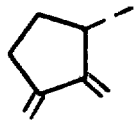

Signed and Sealed this

Thirteenth Day of March 1979

[SEAL]

Attest:

RUTH C. MASON
Attesting Officer

DONALD W. BANNER
Commissioner of Patents and Trademarks